United States Patent
Ewert et al.

(10) Patent No.: US 8,641,902 B2
(45) Date of Patent: Feb. 4, 2014

(54) METHOD FOR WASTEWATER TREATMENT AND WASTEWATER TREATMENT SYSTEM

(75) Inventors: Wolfgang Ewert, Hamburg (DE); Michael Sievers, Clausthal-Zellerfeld (DE); Hinnerk Bormann, Vienenburg (DE)

(73) Assignee: P.C.S. Pollution Control Services GmbH, Hamburg (DE)

( * ) Notice: Subject to any disclaimer, the term of this patent is extended or adjusted under 35 U.S.C. 154(b) by 229 days.

(21) Appl. No.: 12/921,876

(22) PCT Filed: Mar. 6, 2009

(86) PCT No.: PCT/EP2009/001627
§ 371 (c)(1),
(2), (4) Date: Sep. 10, 2010

(87) PCT Pub. No.: WO2009/112208
PCT Pub. Date: Sep. 17, 2009

(65) Prior Publication Data
US 2011/0014684 A1    Jan. 20, 2011

(30) Foreign Application Priority Data
Mar. 12, 2008  (DE) .......................... 10 2008 013 980

(51) Int. Cl.
*C02F 3/00* (2006.01)
*C02F 1/00* (2006.01)
*C02F 9/00* (2006.01)
*C02F 3/12* (2006.01)

(52) U.S. Cl.
USPC ........... 210/613; 210/609; 210/773; 210/259; 210/195.1; 210/253

(58) Field of Classification Search
USPC ......... 210/613, 605, 615, 631, 774, 806, 617, 210/610, 259, 182, 787, 195.1, 253
See application file for complete search history.

(56) References Cited

U.S. PATENT DOCUMENTS

| | | | | |
|---|---|---|---|---|
| 5,888,307 | A  * | 3/1999 | Solheim | 127/37 |
| 6,338,799 | B1 * | 1/2002 | Fukushima et al. | 210/631 |
| 6,444,124 | B1 * | 9/2002 | Onyeche et al. | 210/603 |
| 6,966,989 | B2 * | 11/2005 | Hojsgaard et al. | 210/603 |
| 7,101,482 | B2 * | 9/2006 | Chauzy et al. | 210/605 |
| 7,452,466 | B2 * | 11/2008 | Binning et al. | 210/603 |

FOREIGN PATENT DOCUMENTS

| | | |
|---|---|---|
| DE | 19502856 | 8/1996 |
| EP | 1364915 | 11/2003 |
| FR | 2843106 | 2/2004 |
| GB | 1385915 | 3/1975 |
| WO | WO 93/15818 | 8/1993 |
| WO | WO2005/003044 | 1/2005 |

* cited by examiner

*Primary Examiner* — Nam X. Nguyen
*Assistant Examiner* — Claire Norris
(74) *Attorney, Agent, or Firm* — Whitham, Curtis, Christofferson & Cook, P.C.

(57) ABSTRACT

The invention relates to a method for wastewater treatment utilizing an anaerobic treatment of primary sludge (PS) in a septic tank (5), and a separate treatment of excess sludge (ÜS). The excess sludge (ÜS) is separated from the primary sludge (PS) before the anaerobic treatment, solubilized in a hydrolysis treatment and liquefied, and subjected to a separate anaerobic treatment independently of the primary sludge (PS).

28 Claims, 3 Drawing Sheets

METHOD FOR WASTEWATER TREATMENT AND WASTEWATER TREATMENT SYSTEM

FIELD OF THE INVENTION

The invention relates to a method for wastewater treatment having an anaerobic primary sludge treatment constructed as a two-line system in a digestion vessel and excess sludge separately therefrom in a further digestion vessel.

The invention additionally relates to a wastewater treatment system for treating sludges using such a method, having a digestion vessel for primary sludge and a hydrolysis reactor for the hydrolysis treatment of excess sludge upstream of the anaerobic treatment of excess sludge in the digestion vessel.

BACKGROUND

Essentially two types of sludge occur in municipal and in part also industrial wastewater treatment plants. These two types are the primary or preliminary sedimentation sludge, hereinafter termed primary sludge, and the biological secondary or excess sludge, hereinafter termed excess sludge. In accordance with the current procedure, the chemical sludges scarcely any longer occur separately, but are integrated in the biological sludge by a simultaneous precipitation.

The primary sludge is generally formed by pure gravity sedimentation in settling tanks and can be considered in the anaerobic process as a relatively easily degradable and as a readily dewaterable component in the entire sludge system.

The excess sludge substantially consists of bacterial mass which was substantially formed in the aerobic biological treatment stage and is relatively hard to degrade anaerobically compared with the primary sludge.

Owing to the strong colloidal system and the exopolymeric substances, the excess sludge possesses a high water binding capacity and is considered to be the component in the sludge digestion system which greatly decreases the degree of dewatering according to the proportion.

In the conventional wastewater treatment technique, the two types of sludge, primary sludge and excess sludge, are fed together to the anaerobic degradation stage (in the absence of air) and are digested to completion either mesophilically at 35 to 40° C., or thermophilically at 50 to 58° C. Mixing these sludges comprises two considerable disadvantages:
1. The primary sludge which is in itself readily dewaterable and readily degradable is adversely affected in its properties by an excess sludge proportion, which leads to poorer degradability and a reduction of the capacity in methane formation.
2. On the other hand, excess sludge, in the context of nutrient utilization, is a carrier of valuable material with respect to the possibility of utilizing carbon as methane and recovering as fertilizer the phosphorus which is contained in the excess sludge at 90%. The aim of recovering phosphorus from the excess sludge in a targeted manner can only be achieved economically and expediently if the phosphorus elimination is carried out in the previous wastewater treatment technique by what is termed the BioP method. In this method, no chemical precipitants are added for phosphate precipitation, but the property of the bacterial mass of accumulating polyphosphates to an increased extent under certain process conditions is utilized. Under anaerobic conditions, these polyphosphates are released again as orthophosphate (remobilization). This natural manner of ejecting phosphates from the wastewater opens up economic possibilities of phosphate recovery in the wastewater treatment technique. The phosphates, however, are contained at approximately 90% only in the excess sludge, whereas the primary sludge contains only the approximately 10 to 15% residual phosphates in another form.

During the anaerobic sludge conversion in what are termed the digestion vessels, the carbonaceous compounds are converted to methane ($C_4$), carbon dioxide ($CO_2$), ammonium ($NH_4$) and water, wherein the methane is considered to be a valuable energy carrier and is usually utilized in combined heat and power stations for generating energy and heat. One aim in the optimization in the sludge treatment sector is the greatest possible conversion of the carbon compound in order to achieve maximum reduction in mass of the sludge and to generate maximum energy yield.

After completion of the anaerobic conversion of the mixture of primary and excess sludge, hitherto, after approximately 18 to 30 days, what is termed the digested sludge, using flocculation aids and dewatering machines (centrifuges, sieve belt presses, chamber filter presses etc.), is freed as far as possible from water since the dewatered wastewater sludge is generally used thermally or agriculturally. This is a considerable cost factor for municipalities. For the reduction in costs, attempts are therefore made to concentrate the sludges to the greatest possible extent.

For increasing the anaerobic degree of degradation of the excess sludge, pretreatment methods are known. These mechanical, thermal or else chemical methods by which the excess sludge is disrupted to a certain extent are termed disintegration methods, which can also be used in different combinations. These are used with the aim of disrupting the bacterial mass mechanically, thermally or else chemically to the extent that substrates are as accessible as possible to the anaerobic bacteria and the conversion rates and the conversion velocity are thus considerably increased. The disintegration methods are currently substantially used in the case of excess sludge, wherein after application of the disintegration method in the excess sludge, this is generally mixed again with the primary sludge and they are fed together to the anaerobic process.

The disintegration of wastewater sludge is described, for example, in N. Dichtl, J. Müller, E. Englmann, F. W. Günthert, M. Osswald: "Desintegration von Klärschlammein aktueller Überblick" [Disintegration of wastewater sludge—a current survey], in: Korrespondenz Abwasser 1997 (44), No. 10, pages 1726 to 1739. It is stated that, during the disintegration, the cell walls of the microorganisms in the wastewater sludge are destroyed and the cell contents liberated. The wastewater sludge can thereby be better aerobically or anaerobically stabilized, in such a manner that not only a decrease in the amount of sludge and the digestion time can be achieved, but also an increase in the digester gas production. The purely mechanical disruption of excess sludges leads only to a limited extent to an accelerated and more substantial degradation of the organic material in the digestion.

DE 199 40 994 A1 discloses, in addition, concentrating the predigested raw sludge using a decanter, in such a manner that the solid phase of the digested sludge is separated from a liquid phase.

DE 10 2004 023 171 A1 discloses a method for wastewater treatment in which the biological wastewater treatment is carried out without recirculating the treated excess sludge in the primary sludge. The excess sludge is withdrawn from the primary sludge in a sedimentation device downstream of the biological treatment.

By means of the separate treatment of the excess sludge with ozone and a subsequent aerobic oxidation in a suitable bioreactor, the reactors can be decreased in size and the energy consumption can be reduced.

In addition, EP 0 784 504 B1 discloses a method for hydrolyzing organic materials. By means of the hydrolytic pretreatment of wastewater sludge, breakdown of organic material to smaller particles is achieved, and so a high content of dry matter can be taken from the sludge. The nutrients, owing to the hydrolysis treatment, are in addition more readily accessible to bacteria and the sludge is pasteurized or sanitized.

SUMMARY OF THE INVENTION

Starting therefrom, it is an object of the present invention to provide an improved method for wastewater treatment and a wastewater treatment system therefor with the aim of increasing the energy yield and improving the recovery of valuable materials, such as phosphorus, for example. In addition, the good dewatering property of the primary sludge should be improved.

The object is achieved by the method of the type specified at the outset in that the excess sludge is disrupted and thereby liquefied upstream of the anaerobic treatment by a hydrolysis treatment and, independently of the primary sludge, is subjected to a separate anaerobic treatment.

The anaerobic treatment of the primary sludge therefore takes place separately from the anaerobic treatment of the excess sludge that is taken off. The upstream hydrolysis treatment of the excess sludge means that the pasty excess sludge is liquefied and the water-binding gel substances present in the excess sludge are destroyed by the heating.

At the customary digestion times of 20 days, no differences may be established in the digester gas production between joint and separate anaerobic treatment of excess sludge and primary sludge.

Surprisingly, it has now been shown that separate treatment of hydrolyzed excess sludge on the one hand and primary sludge on the other, in particular at digestion times less than 6 days, causes a higher production of digester gas or methane than the generally conventional joint anaerobic treatment of hydrolyzed excess sludge and primary sludge.

By means of the separate process implementation of the two main sludge types, i.e. the primary sludge and the excess sludge, the individual objectives and the differing characteristics of the sludge types can thereby significantly better be affected. It is possible thereby to make the processes significantly more economical and technically more expedient. As a result, the amounts of sludge to be disposed of can be significantly reduced and the yield of methane and therefore energy can be substantially increased by at least 25 to 40%. The phosphate may also be utilized in a significantly more economical manner and also in a chemically purer form.

The pure primary sludge can be dewatered to 30 to 40% dry residue TR at low usage rates (5 to 8 kg/tonne of dry residue of flocculation aids). The pure completely digested excess sludge, in contrast, would only be able to be dewatered to 16 to 24%. Whereas the conventional mixtures of these two sludges have a degree of dewatering in the range from 20 to 25% dry residue, the proposed separate anaerobic treatment of primary sludge and excess sludge can result in the excess sludge no longer being an interfering component either in the digestion process or in the dewatering process.

At all events, it is first possible by means of the upstream hydrolysis treatment to work up the excess sludge in such a manner, and in the course of this destroy the strongly water-binding hydrogel structure, that the excess sludge can be separately and efficiently degraded in a downstream anaerobic treatment step.

As a result, the separate anaerobic treatment of primary sludge and the hydrolyzed excess sludge means that the methane yield and the degree of degradation are considerably increased.

The hydrolysis treatment of the excess sludge preferably proceeds thermally. In this case, the excess sludge can be heated to a temperature in the range from 130 to 180° C. After disruption of the heated excess sludge, which proceeds by the excess sludge residing in a pressurized reactor under the action of heat for approximately 15 to 45 minutes, for example, the heated excess sludge is expanded, which ensures destruction of the bacterial cells and thereby further mechanical disruption.

The hydrolysis can be carried out by steam injection into the excess sludge, via heat exchangers or by other energy carriers.

It is particularly advantageous if, before the hydrolysis treatment, the excess sludge is homogenized, for example using a homogenizer having a pressure of 40 to 500 bar. By means of the homogenization, the efficiency of the subsequent hydrolysis method is achieved owing to the homogeneous distribution of the components in the excess sludge.

After the hydrolysis treatment, the hydrolyzed excess sludge is cooled, preferably to a temperature in the range from 30 to 55° C., particularly preferably in the range from 35 to 38° C. The excess sludge cooled to this temperature is then fed to the separate anaerobic treatment.

The anaerobic treatment takes place particularly preferably in a fixed-bed reactor or fluidized-bed reactor, such as, for example, a pellet reactor. Such fixed-bed reactors or fluidized-bed reactors are known from food technology. These types of reactors have hitherto only been able to be used with very low-viscosity, water-like wastewaters or process waters, since they are very substantially dependent, inter alia, on the mobility of the pellets (floating and swirling) in the reactor. The conventional excess sludge, in thickened form, however, is present in somewhat pasty form, and so when flowing through the pellet reactor the pellets, owing to the high viscosity of the sludge medium to be treated, would be discharged and would be unable to be retained in the reactor.

Owing to the upstream hydrolysis, inter alia, also the gel structure, and therefore the viscosity, of the sludge are destroyed, and so this is so greatly reduced that the excess sludge can be treated in a pellet reactor at the prevailing concentration.

A high carbon conversion rate and a high reaction velocity can be achieved thereby. The reason for this is the disruption of the excess sludge by means of the thermal hydrolysis and the utilization of the specific high conversion rates of a pellet reactor which, in contrast to a completely mixed conventional anaerobic reactor, only requires residence times between 5 and 20 hours in order to achieve a carbon conversion rate to methane which would require 20 days on average in a conventional reactor.

By charging the fixed-bed reactor or fluidized-bed reactor exclusively with the hydrolyzed excess sludge, the bacterial mass can adapt significantly better to the uniform substrate, since a higher specialization toward the methane-forming bacteria takes place (avoidance of the biological competition situation). The rate-determining step of the biological hydrolysis is omitted in this case, since the substrate is already present in hydrolyzed form, and so the anaerobic conversion is favored.

The anaerobically treated excess sludge can subsequently be filtered, centrifuged and/or precipitated in order to extract solids and/or recover raw materials such as, for example, phosphates. By means of the separate treatment of the excess sludge, the solids extraction and raw material recovery may be made significantly more economical and chemically purer. The reason is in turn the uniformity of substance and improvement of disruption achieved by the separation of excess sludge and primary sludge.

The extracted solids can be fed to the primary sludge before or during the separate anaerobic treatment of the primary sludge and can be further degraded together with the primary sludge. These solids do not impair the quality of the primary sludge. Rather they lead to concentration and thereby to improved degradability of the primary sludge in contrast to the hydrogel-like, water-binding excess sludge.

The heat energy occurring during the hydrolysis of the excess sludge, for example in the expansion operation, can be further utilized in the process. It is particularly advantageous when the heat energy is used for sanitizing the primary sludge, before the primary sludge is anaerobically treated. The sanitation requirements of the primary sludge can thereby be met using the heat from the process for treating the excess sludge.

The object is additionally achieved by the wastewater treatment system of the type specified at the outset in that a separate reactor is provided for the anaerobic treatment of the hydrolyzed excess sludge, said reactor being connected so as to communicate directly or indirectly with the outlet of the hydrolysis reactor.

BRIEF DESCRIPTION OF THE DRAWINGS

The invention will be described in more detail hereinafter with reference to an exemplary embodiment with the accompanying drawing. In the drawings.

DETAILED DESCRIPTION OF THE INVENTION

Figure 1:
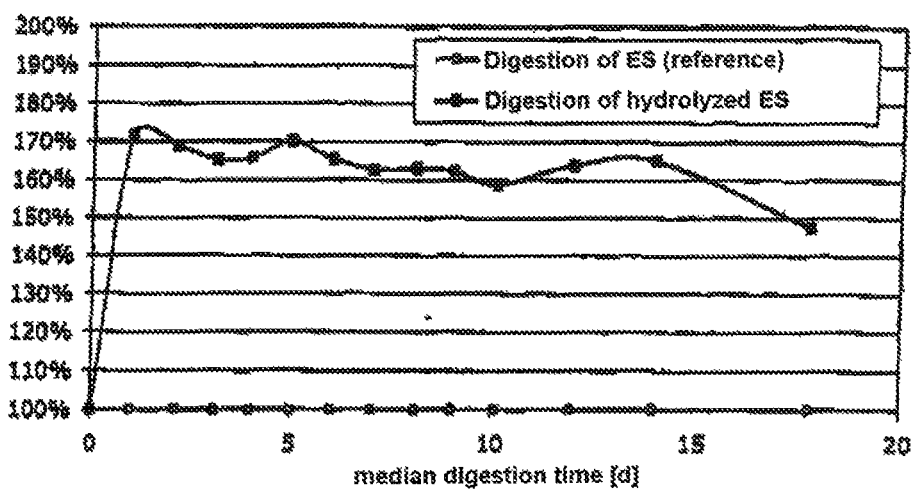
FIG. 1 shows a diagram of the digestion of excess sludge compared with the digestion of hydrolyzed excess sludge over a median digestion time.

FIG. 1 illustrates by way of example the increase in digester gas or methane production due to thermal hydrolysis of the pure excess sludge depending on the digestion time. It is possible to see an approximately 70% increase of the total digester gas or total methane production and the subsequent slight decrease of the total methane production for the hydrolyzed excess sludge. At a sufficiently long digestion time, for both sludges according to general theory approximately equally as much digester gas or methane should be produced. However, in practice, this is generally not achieved.

Figure 2:
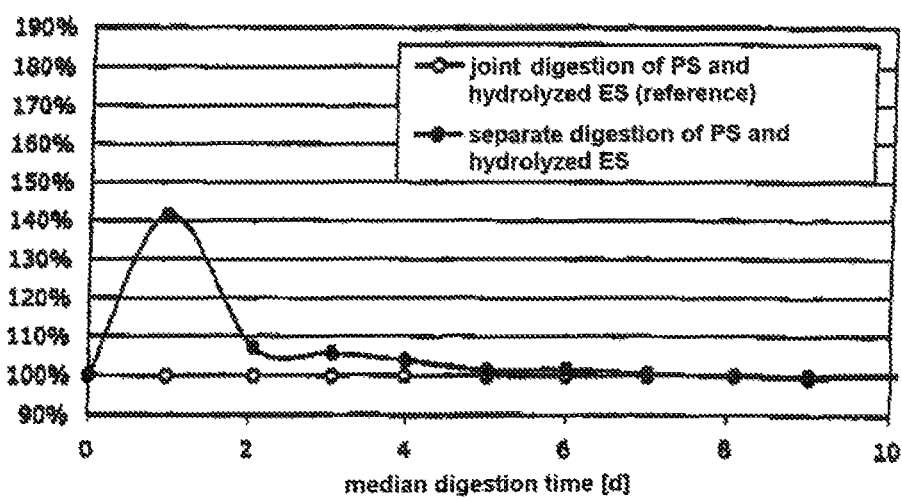
FIG. 2 shows a diagram of the joint digestion of primary sludge and excess sludge compared with the separate digestion of primary sludge and hydrolyzed excess sludge versus a median digestion time.
Figure 3:
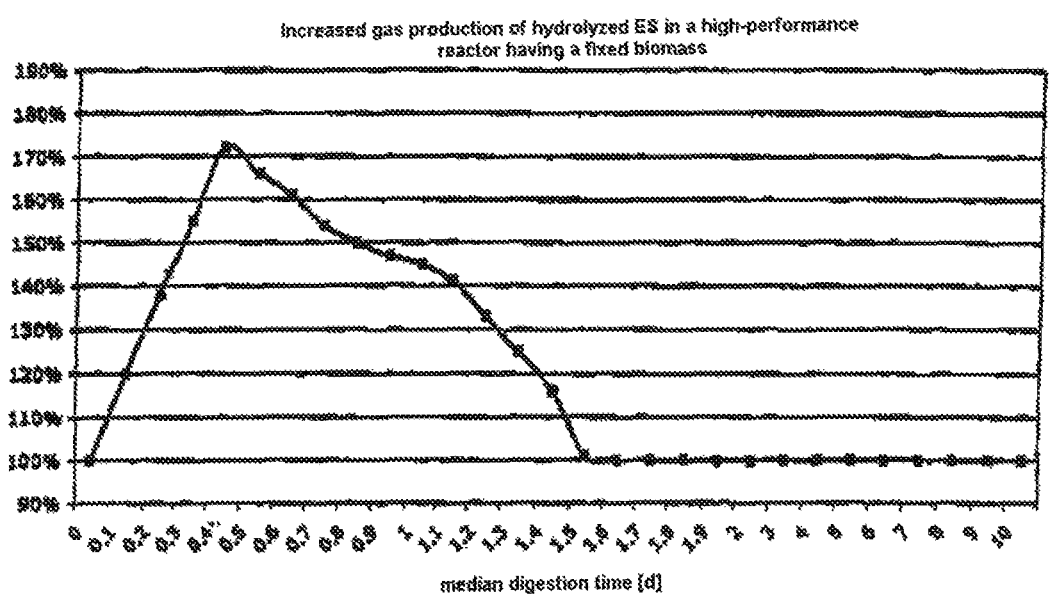
FIG. 3 shows a diagram of the increased gas production of hydrolyzed excess sludge in a high performance reactor having a fixed biomass versus a median digestion time.

FIG. 2 shows the result of a shared anaerobic treatment (reference) of hydrolyzed excess sludge and primary sludge compared with the result of a separate anaerobic conversion, in a conventional digestion vessel customary on wastewater treatment systems, of hydrolyzed excess sludge on the one hand and primary sludge on the other, wherein the digester gas production of the two separate digestion stages has been added. Surprisingly, it has been found that not only the already known 50 to 70% increase of digester gas production of the excess sludge fraction is possible by thermal hydrolysis, but in addition a still further increase by up to approximately 40%, in particular at very short digestion times of less than 2 days owing to a separate anaerobic treatment of pure excess sludge on the one hand and primary sludge on the other. When what is termed an anaerobic high-performance reactor (fixed-bed or pellet reactor) is used, the effect of the increased gas production with separate treatment of the hydrolyzed excess sludge in relation to the gas yield and also in relation to the conversion velocity is considerably increased. In the calculation of the energy yield, the significantly higher methane content with these reactor types must be taken into account. An example is shown in FIG. 3. This makes it clear that separate treatment of hydrolyzed excess sludge on the one hand and primary sludge on the other, in particular for digestion times less than 6 days, causes a higher digester gas or methane production than the generally customary joint anaerobic treatment of hydrolyzed excess sludge and primary sludge.

Figure 4:
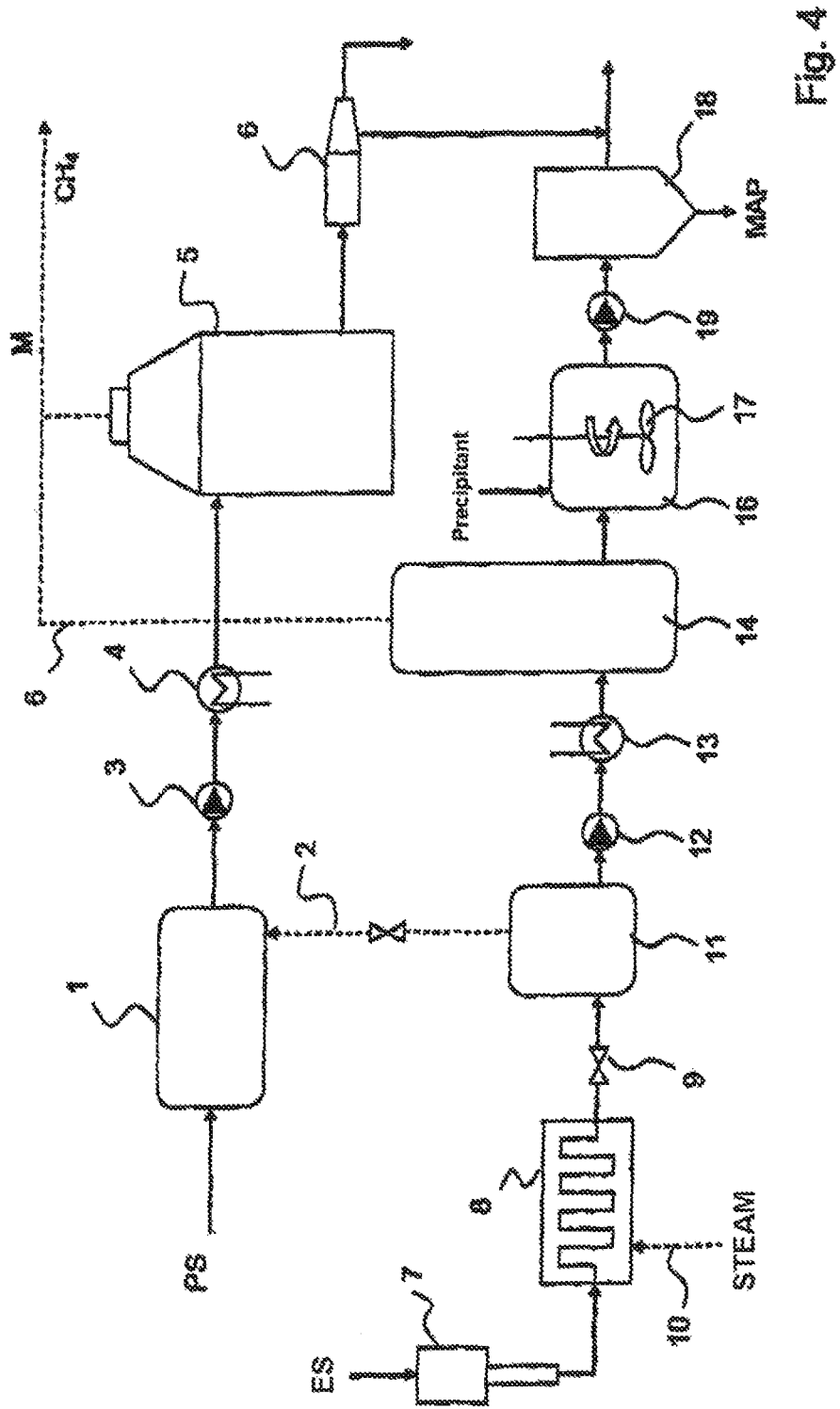
FIG. 4 shows a sketch of a wastewater treatment system having a flow diagram of the materials streams.

FIG. 4 shows a diagrammatic sketch of a wastewater treatment system having the materials streams flowing through the individual appliances.

Primary sludge PS is fed to a sanitation vessel 1 which is equipped in a manner known per se for heating and sanitation of the primary sludge PS kept in the sanitation vessel 1 for a sanitation time. The heating proceeds by feeding heat energy via a line 2 for a heat conduction medium such as, for example, steam or water. After the sanitation of the primary sludge PS in the sanitation vessel 1 it is conducted into a digestion vessel 5 for anaerobic treatment via a pump 3 and a heat exchanger 4. In the digestion vessel 5 the primary sludge PS is digested to completion, wherein methane gas M is formed, which can be removed for further use, for example in a combined heat and power station (which is not shown).

After the digestion to completion, the digested sludge DS formed from the primary sludge PS is taken off and dewatered using a dewatering unit 6 such as, e.g., using a flocculation reactor, with the aid of flocculants.

In a separate processing train, excess sludge ES is first homogenized in a homogenizer 7 at a pressure of 40 to 500 bar. The excess sludge ES has previously been taken off from the primary sludge PS and thickened to approximately 6 to 12% dry residue TR. The homogenized excess sludge ES is then fed to a hydrolysis reactor 8 for the hydrolysis treatment. In the hydrolysis reactor 8 the excess sludge ES will be disrupted for a period of approximately 15 to 45 minutes at a temperature in the range from 130 to 180° C. A pressure retention valve 9 ensures maintenance of the pressure and temperature conditions. The hydrolysis reactor 8 can be heated with steam as shown by injecting steam directly into the excess sludge ES via a steam line 10. However, the heat can also be introduced via heat exchangers or using other energy carriers.

After disruption of the excess sludge ES in the hydrolysis (pressure) reactor 8, the excess sludge ES is abruptly expanded into an expansion tank 11 by opening the pressure retention valve 9. This ensures destruction of the bacterial cells and causes further mechanical disruption of the excess sludge ES. In the expansion tank 11, the excess sludge ES then has a temperature of approximately 90 to 100° C. Via a pump 12, the excess sludge ES is then fed to a heat exchanger 13 in which the excess sludge ES is cooled to the desired anaerobic reactor temperature of preferably 35 to 38° C.

The excess energy arising in the expansion and the heat exchanger can be usefully used again at another point of the process.

Therefore it is advantageous if the line 2 leading into the sanitation vessel 1 is connected to the expansion tank 11 in order to heat up in the expansion tank 11 the heating medium transported via the line 2 to the sanitation vessel 1. Alternatively, or in addition, the heat conduction medium transported in the line 2 can also be heated up via the heat exchanger 13.

The cooled hydrolyzed excess sludge ES is passed separately from the primary sludge PS to a reactor 14 for the anaerobic treatment of the excess sludge ES. This anaerobic reactor 14 is not as in the conventional municipal wastewater treatment technique a fully mixed reactor in which the bacterial mass is not present in suspended form, but is constructed as a fixed-bed or fluidized-bed reactor in the form of a pellet reactor in which the bacterial mass is present to a certain extent in a fixed form. These pellet reactors are known from industry, e.g. papermaking or food industry, and are used there.

Whereas the conventional excess sludge ES is pasty in thickened form, owing to the upstream hydrolysis, the gel structure, inter alia, is also destroyed and therefore the viscosity of the excess sludge ES is decreased, and so the hydrolyzed excess sludge ES can now be treated in the anaerobic reactor 14. The treatment time is less than 5 to 6 days, preferably about 5 to 20 hours, wherein the methane streams formed during the anaerobic treatment are removed via a methane gas line 15 for further use together with the methane gas M from the digestion vessel 5 for the primary sludge PS. The methane gas M should be, as is customary, purified, desulfurized, dehumidified and then fed to a gas storage vessel.

After completion of the anaerobic process in the anaerobic reactor 14, a low-viscosity mass that is very reduced in carbon content is then present which contains only very few solids and can very readily be further processed. According to solids content and further objective, before the entry and after the exit of the hydrolyzed or digested excess sludge ES into/from the anaerobic reactor 14, the solids still present can be separated off by suitable filters and centrifuges, so the remaining low-solids water is outstandingly suitable for recovery of raw materials, in particular phosphates, or also nitrogenous products.

The phosphates can be recovered in various ways. Preferably, a precipitation unit 16 having a stirrer 17 is connected to the outlet of the anaerobic reactor 14 which precipitation unit 16 is equipped, e.g., for precipitating magnesium ammonium phosphate MAP from the prepared excess sludge ES by adding magnesium salts such as, e.g. magnesium chloride, and setting an appropriate pH of 7.5 to 7.8. The poorly soluble magnesium ammonium phosphate MAP precipitates out in the precipitation unit 16 and, in a subsequent sedimentation vessel 18 which is connected to the precipitation unit 16 via a pump 19, can be sedimented and extracted. The water passed out of the sedimentation vessel 18 is then low in carbon and phosphorus. It can be further treated separately or together with the water separated off from the primary sludge by the dewatering unit 6, for example for eliminating nitrogen N. These measures are known per se.

The solids optionally separated off downstream of the anaerobic reactor 14, on account of the upstream hydrolysis, are very substantially free from water-binding gel substances and can be added to the conventional digestion vessel 5 for the primary sludge PS without risk, without in this case giving rise to the adverse effects of more difficult sludge dewatering. At the same time, the still reactive carbon compounds were converted together with the primary sludge PS to methane.

By means of the separate anaerobic treatment of the excess sludge ES it is possible, with the aid of the upstream hydrolysis, not only to reduce the excess sludge ES as known hitherto by ozone addition, but to utilize the excess sludge ES more efficiently for energy and raw material recovery.

The upstream hydrolysis has the further effect that the crystallization of the phosphates that occurs hitherto in the digestion vessel 5 and the subsequent dewatering unit 6 is prevented. This is because the phosphates are substantially present in the excess sludge ES, which is treated separately, wherein the anaerobic reactor 14 has a lower pH for the excess sludge ES than the pH present in the digestion vessel 5 for the primary sludge PS.

In the anaerobic reactor 14 for the excess sludge ES, immobilized biomass can be used, owing to the homogeneous structure of the hydrolyzed excess sludge ES, which leads to a higher conversion rate and velocity during the anaerobic treatment. For the anaerobic treatment of the primary sludge PS, which is a suspension, in contrast, suspended biomass is used which gives rise to a lower conversion rate and a longer treatment time.

The invention claimed is:

1. A method for wastewater treatment comprising the steps of:
   taking off excess sludge (ES) from primary sludge (PS), and then
   anaerobically treating said primary sludge (PS) in a digestion vessel and
   separately treating said excess sludge (ES), wherein the excess sludge (ES) is disrupted and liquefied in a hydrolysis treatment and, independently of the primary sludge (PS), subjected to a separate anaerobic treatment such that the anaerobic treatment of primary sludge (PS) takes place separately from the anaerobic treatment of the excess sludge (ES).

2. The method as claimed in claim 1, wherein the hydrolysis treatment comprises one or more of thermal and chemical hydrolysis of the excess sludge (ES).

3. The method as claimed in claim 2, wherein the thermal hydrolysis comprises the steps of heating the excess sludge (ES) to a temperature in the range from 130 to 180° C., disrupting the heated excess sludge (ES) in a hydrolysis reactor, and expanding the heated excess sludge (ES) after a residence time in the hydrolysis reactor.

4. The method as claimed in claim 3, wherein the residence time of the excess sludge (ES) in the hydrolysis reactor for disruption of cells is 15 to 60 minutes.

5. The method as claimed in claim 1, further comprising the step of injecting steam into the excess sludge (ES) for the hydrolysis treatment.

6. The method as claimed in claim 2, further comprising the steps of raising the pH of the excess sludge (ES) to values between 9 and 14 and increasing the temperature to 50 to 130° C. for the one or more of chemical and thermal hydrolysis.

7. The method as claimed in claim 1, further comprising the step of homogenizing the excess sludge (ES) before the hydrolysis treatment.

8. The method as claimed in claim 1, further comprising the step of cooling the hydrolyzed excess sludge (ES) to a temperature in the range from 30 to 55° C.

9. The method as claimed in claim 1, wherein the anaerobic treatment of the hydrolyzed excess sludge (ES) in the separately treating step proceeds in a fixed-bed reactor or a fluidized-bed reactor.

10. The method as claimed in claim 9, wherein the fixed-bed reactor or fluidized-bed reactor is a pellet reactor.

11. The method as claimed in claim 1, further comprising filtering, centrifuging and/or precipitating the anaerobically treated excess sludge (ES) for extracting solids and/or recovering raw materials.

12. The method as claimed in claim 11, further comprising the step of feeding solids separated off from the anaerobically treated excess sludge (ES) to the primary sludge (PS) before or during the separate anaerobic treatment of the primary sludge (PS).

13. The method as claimed in claim 1, further comprising the step of heating the primary sludge (PS) for sanitation by means of heat energy occurring on hydrolysis of the excess sludge (ES).

14. The method as claimed in claim 1, wherein the anaerobic treatment of the hydrolyzed excess sludge (ES) in the separately treating step is carried out for a time of less than 5 days.

15. The method as claimed in claim 1, further comprising the step of discharging, for further use, methane gas (M) occurring from the anaerobic treatment of the primary sludge (PS) and the separate anaerobic treatment of the excess sludge (ES).

16. A wastewater treatment system for treating at least one of wastewaters and sludges comprising
    separate processing trains for excess sludge (ES) and primary sludge (PS)
    a digestion vessel in said processing train for said primary sludge (PS) for anaerobic treatment of said primary sludge (PS) after taking off said excess sludge (ES) from said primary sludge (PS),
    a hydrolysis reactor in said processing train for said excess sludge (ES) for the hydrolysis treatment of excess sludge (ES) taken off said primary sludge (PS), wherein the excess sludge (ES) is disrupted and liquefied, and
    a separate reactor for the anaerobic treatment of hydrolyzed excess sludge (ES) such that the anaerobic treatment of the primary sludge (PS) takes place separately from the anaerobic treatment of the excess sludge (ES), said reactor being connected so as to communicate directly or indirectly with the outlet of the hydrolysis reactor.

17. The wastewater treatment system as claimed in claim 16, further comprising
    a homogenizer for disintegrating the excess sludge (ES), said homogenizer being connected upstream of the hydrolysis reactor.

18. The wastewater treatment system as clainied in claim 16, wherein the separate reactor for the anaerobic treatment of hydrolyzed excess sludge (ES) is a fixed-bed reactor or a fluidized-bed reactor.

19. The wastewater treatment system as claimed in claim 18, wherein the fixed-bed reactor or fluidized-bed reactor is a pellet reactor.

20. The wastewater treatment system as claimed in claim 16, wherein the hydrolysis reactor has a downstream expansion tank.

21. The wastewater treatment system as claimed in claim 16, further comprising
    a precipitation unit following downstream of an outlet of the separate reactor for the anaerobic treatment of the excess sludge (ES), said precipitation unit having a feed for precipitant for precipitating phosphates from the hydrolyzed and anaerobically treated excess sludge (ES).

22. The wastewater treatment system as claimed in claim 16, further comprising
    one or more of a centrifuge and filter for separating off solids from the hydrolyzed and anaerobically treated excess sludge (ES), said one or more centrifuge and filter following downstream of the outlet of the separate reactor for the anaerobic treatment of the excess sludge (ES).

23. The wastewater treatment system as claimed in claim 16, further comprising
    a line for heat conduction medium between the expansion tank and a sanitation vessel for primary sludge (PS), wherein the sanitation vessel has a heating unit for heating primary sludge (PS) by means of heat energy which can be transferred by the heat conduction medium from the expansion tank via the line.

24. The wastewater treatment system as claimed in claim 16, further comprising
    a heat exchanger between the hydrolysis reactor and the separate reactor for the anaerobic treatment of the hydrolyzed excess sludge (ES) for cooling the excess sludge (ES).

25. The method as claimed in claim 4, wherein said residence time is from 15 to 45 minutes.

26. The method as claimed in claim 6, wherein the pH of the excess sludge (ES) is raised to values between 9 and 12 and the temperature is increased to 60 to 100° C. for the one or more of chemical and thermal hydrolysis.

27. The method as claimed in claim 8, wherein said cooling is to a temperature in the range from 35 to 38° C.

28. The method as claimed in claim 14, wherein said anaerobic treatment is carried out for a time of 5 to 20 hours.

* * * * *